US012134618B2

(12) United States Patent
Oppenheimer et al.

(10) Patent No.: US 12,134,618 B2
(45) Date of Patent: Nov. 5, 2024

(54) METHOD OF PREPARATION OF FLORASULAM

(71) Applicant: Dow AgroSciences LLC, Indianapolis, IN (US)

(72) Inventors: Jossian Oppenheimer, Midland, MI (US); Michael Gullo, Midland, MI (US); David E. Podhorez, Midland, MI (US); Justin A. Alberts, Midland, MI (US)

(73) Assignee: Corteva Agriscience LLC, IN (US)

( * ) Notice: Subject to any disclaimer, the term of this patent is extended or adjusted under 35 U.S.C. 154(b) by 254 days.

(21) Appl. No.: 16/754,856

(22) PCT Filed: Oct. 10, 2018

(86) PCT No.: PCT/US2018/055115
§ 371 (c)(1),
(2) Date: Apr. 9, 2020

(87) PCT Pub. No.: WO2019/074995
PCT Pub. Date: Apr. 18, 2019

(65) Prior Publication Data
US 2021/0198262 A1    Jul. 1, 2021

Related U.S. Application Data

(60) Provisional application No. 62/570,271, filed on Oct. 10, 2017.

(51) Int. Cl.
*A01N 43/90* (2006.01)
*C07D 487/04* (2006.01)

(52) U.S. Cl.
CPC .......... *C07D 487/04* (2013.01); *A01N 43/90* (2013.01)

(58) Field of Classification Search
None
See application file for complete search history.

(56) References Cited

U.S. PATENT DOCUMENTS

| 4,818,273 A * | 4/1989 | Kleschick ............. C07C 205/38 |
| | | 548/173 |
| 4,910,306 A | 3/1990 | McKendry |
| 5,959,106 A | 9/1999 | Pearson et al. |
| 5,959,196 A | 9/1999 | Pearson et al. |
| 2003/0050193 A1 | 3/2003 | Bieringer et al. |
| 2019/0106428 A1 | 4/2019 | Oppenheimer et al. |

FOREIGN PATENT DOCUMENTS

| CN | 103509027 A | 1/2014 |
| CN | 103509027 B | 1/2016 |
| WO | 2019074995 A1 | 4/2019 |

OTHER PUBLICATIONS

Dow Agrosciences LLC, Non-Final Office Action, Apr. 18, 2019, U.S. Appl. No. 16/155,905 (Oct. 10, 2018).
International Search Report, PCT/US2018/055115, Dec. 7, 2018, Dow AgroSciences LLC.
Extended European Search Report for European Application No. 18866958.4, mailed May 7, 2021, 06 Pages.
International Preliminary Report on Patentability for International Application No. PCT/US2018/055115, mailed Apr. 23, 2020, 07 Pages.

* cited by examiner

*Primary Examiner* — Bethany P Barham
*Assistant Examiner* — Barbara S Frazier

(57) ABSTRACT

The present disclosure concerns a method for preparing florasulam which involves treating a solution of 2,6-difluoroaniline in 1,2-propylene glycol with: a) sulfonyl chloride III and then b) a base to provide, after workup and isolation, florasulam (I) in yields of about 65-85%. The treatment of 2,6-difluoroaniline with sulfonyl chloride III and the base are conducted by controlled additions.

18 Claims, No Drawings

METHOD OF PREPARATION OF FLORASULAM

CROSS-REFERENCE TO RELATED APPLICATIONS

This application claims priority to International (PCT) Patent Application Serial No. PCT/US2018/055115, filed Oct. 10, 2018, and entitled "METHOD OF PREPARATION OF FLORASULAM," which claims priority to U.S. Provisional Application Ser. No. 62/570,271, filed on Oct. 10, 2017, the entire disclosure of which is hereby expressly incorporated by reference.

FIELD OF THE INVENTION

An improved method of preparing florasulam is described. The method includes the use of modified reaction conditions for the sulfonamide coupling reaction.

BACKGROUND OF THE INVENTION

Florasulam (N-(2,6-difluorophenyl)-8-fluoro-5-methoxy[1,2,4]triazolo[1,5-a]pyrimidine-2-sulfonamide, I) is a herbicide marketed by Dow AgroSciences LLC. The final step of the manufacturing process for florasulam, as described in U.S. Pat. No. 5,959,106, involves the coupling of 2,6-difluoroaniline (II) with 8-fluoro-5-methoxy[1,2,4]triazolo[1,5-a]pyrimidine-2-sulfonyl chloride (III) to afford the sulfonamide product florasulam (I) as shown in Scheme 1.

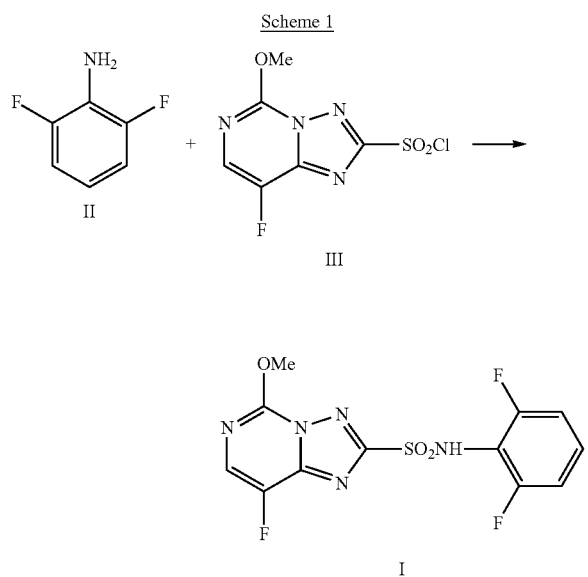

In order to obtain commercially acceptable yields, the molar ratio of the difluoroaniline (II) to the sulfonyl chloride (III) in the reaction is from about 2.2 to about 5, preferably from about 2 to about 3. However, the use of excess amounts of the costly 2,6-difluoroaniline (II) increases the cost of manufacturing florasulam by this method.

Chinese Patent Application No. CN103509027A describes methods for preparing florasulam. The reaction scheme is shown in Scheme 2.

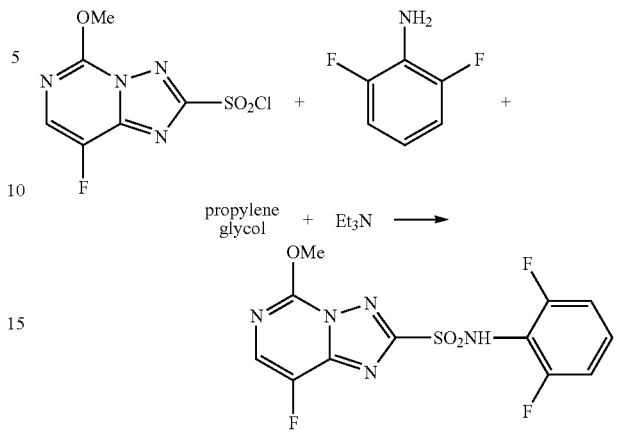

The modified reaction conditions described therein involve a one pot procedure using a base, such as triethylamine, to allegedly reduce the amount of the costly 2,6-difluoroaniline (II) used in the method to from about 1 to about 1.5 molar equivalents. However, this method fails to provide florasulam in the high yields that are reported as shown in the examples below.

It is highly desirable to have a method of preparing florasulam that reduces the amount of 2,6-difluoroaniline used in the coupling reaction while maintaining/improving commercially acceptable yields. Such a method could decrease the cost of manufacturing florasulam by reducing the use of an expensive raw material.

SUMMARY

Described herein is an improved method of preparing florasulam (I). The improved method involves coupling 2,6-difluoroaniline (II) with 8-fluoro-5-methoxy[1,2,4]triazolo[1,5-a]pyrimidine-2-sulfonyl chloride (III) using conditions that provide florasulam in high yield at a lower cost. The improved method uses less 2,6-difluoroaniline than previous methods and produces florasulam in high yield. The coupling reaction employs from about 1 to about 2 molar equivalents of 2,6-difluoroaniline and from about 0.5 to about 1.5 molar equivalents of a base, relative to the amount of sulfonyl chloride III used.

The method involves treating a solution of 2,6-difluoroaniline in propylene glycol with: a) sulfonyl chloride III and then b) a base to provide, after workup and isolation, florasulam (I) in yields of about 65 to about 85%. The treatments with sulfonyl chloride III and the base are conducted by controlled additions.

For example, in one embodiment of the method, 8-fluoro-5-methoxy[1,2,4]triazolo[1,5-a]pyrimidine-2-sulfonyl chloride is added to a mixture of 2,6-difluoroaniline and 1,2-propylene glycol, a base is then added to the resulting mixture, and florasulam is isolated from the final mixture. In another embodiment of the method, 8-fluoro-5-methoxy[1,2,4]triazolo[1,5-a]pyrimidine-2-sulfonyl chloride is added in a controlled manner to a mixture of 2,6-difluoroaniline and 1,2-propylene glycol, a base is then added to the resulting mixture, and florasulam is isolated from the final mixture.

In another embodiment of the method, 8-fluoro-5-methoxy[1,2,4]triazolo[1,5-a]pyrimidine-2-sulfonyl chloride is added to a mixture of 2,6-difluoroaniline and 1,2- propylene glycol, a base is then added to the resulting mixture in a controlled manner, and florasulam is isolated from the final mixture. In another embodiment of the new method, 8-fluoro-5-methoxy[1,2,4]triazolo[1,5-a]pyrimidine-2-sulfonyl chloride is added to a mixture of 2,6-difluoroaniline and 1,2-propylene glycol at between about 15° C. to about 35° C., a base is then added to the resulting mixture at between about 15° C. to about 35° C., and florasulam is isolated from the final mixture.

DETAILED DESCRIPTION

Improved methods of preparing florasulam (I) are described herein. The improved method involves coupling 2,6-difluoroaniline (II) with 8-fluoro-5-methoxy[1,2,4]triazolo[1,5-a]pyrimidine-2-sulfonyl chloride (III) using conditions to provide florasulam in high yield at a lower cost. The methods use less 2,6-difluoroaniline. The coupling reaction employs from about 1 to about 2 molar equivalents of 2,6-difluoroaniline and from about 0.5 to about 1.5 molar equivalents of a base, relative to the amount of sulfonyl chloride III used.

The improved method is shown in Scheme 3. Specifically, the method involves treating a solution of 2,6-difluoroaniline II in 1,2-propylene glycol with: (a) sulfonyl chloride III followed by (b) a base to provide, after workup and isolation, florasulam (I) in yields of about 65-85%. The additions of sulfonyl chloride III and the base are conducted by controlled addition.

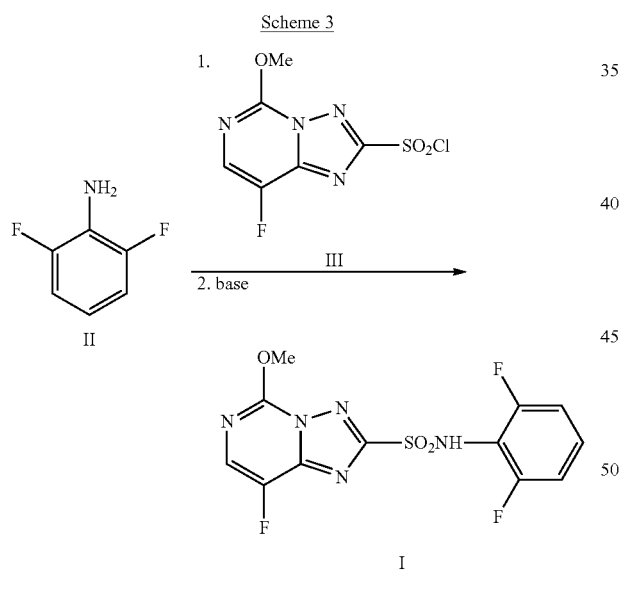

Scheme 3

I. Definitions

"Controlled addition" or "controlled adding," as used herein, refers to controlling the rate at which a chemical is added to a reaction vessel containing other chemicals in order to achieve temperature control, sufficient physical mixing, and/or efficient reaction rates for the chemistry that is being conducted in the reaction vessel. Controlled addition or adding is the opposite of uncontrolled addition or adding such as the rapid contacting of reactants. Controlled addition (or adding) may also be referred to as slow addition, continuous addition (i.e., con-addition), metered addition, portion-wise addition, addition in a controlled manner, and the like.

In some embodiments, the controlled addition or con-trolled adding of a reactant in the described method may be conducted over a period of at least about 0.5 hours, at least about 0.75 hours, at least about 1 hour, at least about 1.5 hours, at least about 2 hours, at least about 2.5 hours, at least about 3 hours, at least about 3.5 hours, at least about 4 hours, at least about 4.5 hours, or at least about 5 hours.

II. Process Variables

A. Order of Controlled Addition of Reactants

In some embodiments, the order of addition of reactants and the controlled additions of those reactants in the method are used to obtain high yields of florasulam. Sulfonyl chloride III should be added to a solution of 2,6-difluoroaniline (II) in the solvent in a controlled manner to achieve high yields of florasulam. The addition of the base to the mixture formed by adding III to II can also be done by a controlled addition. Failure to follow the order of addition and/or controlled additions of the reactants, and instead use of rapid contacting/mixing of all reactants and the solvent, can lead to poor yields of florasulam. In some embodiments, the base may be combined with the solution of 2,6-difluoroaniline (II) and the solvent to form a mixture before controlled addition of sulfonyl chloride III to the mixture.

B. Bases

Bases for use in the described method may be selected from the group including organic bases, inorganic bases, partially inorganic bases, and combinations thereof.

Suitable organic bases include, but are not limited to, trialkylamines, such as triethylamine, aromatic amines such as pyridine, heterocyclic amines such as imidazole, N-methylimidazole and benzimidazole, and bicyclic amines such as 1,4-diazabicyclo[2.2.2]octane and 1,8-diazabicyclo[5.4.0]undec-7-ene.

Suitable inorganic and partially inorganic bases may include, but are not limited to, monobasic salts of organic diacids such as potassium hydrogen tartrate and potassium hydrogen phthalate, carbonate and bicarbonate salts such as sodium and potassium carbonate and sodium and potassium bicarbonate, and salts of monoacids such as sodium and potassium acetate.

C. Solvents

Solvents for use in the described method include those of Formula IV

IV wherein X represents fluoromethyl, difluoromethyl, trifluoromethyl, chloromethyl, dichloromethyl, trichloromethyl, 1,1-difluoroethyl, hydroxymethyl, 1-hydroxyethyl, methoxymethyl, or cyanomethyl, and R represents hydrogen, methyl, or fluoromethyl. 1,2-Propanediol (1,2-propylene glycol), 1,2-ethanediol (ethylene glycol), and 2,2,2-trifluoroethanol are often more preferred. In some embodiments, the solvent is 1,2-Propanediol due to its performance in the method, its low cost, and its low toxicity.

The alcohol of Formula IV employed can be used alone as the organic solvent medium or can be part of an organic solvent medium that includes other alcohols of Formula I and/or inert organic solvents. Inert solvents that can be employed in conjunction with the alcohols of Formula IV include chlorinated aliphatic solvents, such as dichloromethane, 1,2-dichloroethane, tetrachloroethylene, chloroform, and 1,1,1-trichloroethane; chlorinated aromatic solvents, such as 1,2-dichlorobenzene; aromatic hydrocarbons, such as benzene, toluene, and xylene; nitriles, such as acetonitrile; esters, such as ethyl acetate; and ethers, such as 1,2-dimethoxyethane and tetrahydrofuran. Inert organic solvents in which the 8-fluoro-5-methoxy[1,2,4]triazolo[1,5-a]pyrimidine-2-sulfonyl chloride compound of Formula III are at least somewhat soluble are generally preferred (when an inert organic solvent is used) and dichloromethane is typically more preferred. It is often preferred to carry out the method in the presence of the alcohol as the only organic solvent in the medium; that is, without the addition of other inert organic solvents.

The amount of organic solvent medium employed is an amount that facilitates mixing and contact of the reagents as well as heat transfer and that supplies an appropriate amount of the alcohol of Formula IV in relationship with the amount of the 8-fluoro-5-methoxy[1,2,4]triazolo[1,5-a]pyrimidine-2-sulfonyl chloride compound of Formula III being used in the method. An amount of alcohol sufficient to give a suitably rapid reaction rate, but not so much as to create a problem in product isolation or extra cost in recycle efforts should be employed. The reaction rate typically increases as the amount of alcohol in the system increases, but recovery of the desired product becomes more difficult and expensive. An appropriate amount of the alcohol of Formula IV is generally from at least about 0.3 parts to about 5 parts by weight of alcohol per part of the 8-fluoro-5-methoxy[1,2,4]triazolo[1,5-a]pyrimidine-2-sulfonyl chloride compound of compound of Formula III used. Amounts between about 0.5 and about 3.0 are generally more preferred.

D. Molar Equivalents of Reactants

The ratio of molar equivalents of 2,6-difluoroaniline (II) relative to 8-fluoro-5-methoxy[1,2,4]triazolo[1,5-a]pyrimidine-2-sulfonyl chloride (i.e., sulfonyl chloride III) used in the described method may be from about 1:1 to about 2:1. This ratio may be about 1.1:1, about 1.2:1, about 1.3:1, about 1.4:1, about 1.5:1, about 1.6:1, about 1.7:1, about 1.8:1, or about 1.9:1.

The ratio of molar equivalents of the base relative to 8-fluoro-5-ethoxy[1,2,4]triazolo-[1,5-a]pyrimidine-2-sulfonyl chloride (i.e., sulfonyl chloride III) used in the described method may be from about 0.5:1 to about 1.5:1. This ratio may be about 0.6:1, about 0.7:1, about 0.8:1, about 0.9:1, about 1:1, about 1.1:1, about 1.2:1, about 1.3:1, or about 1.4:1.

E. Temperature

The temperature range to use in the described processes when combining the reactants together is very important for obtaining high yields of florasulam. Combining 2,6-difluoroaniline in 1,2-propylene glycol with: a) sulfonyl chloride III and then b) a base must be conducted under very temperature controlled conditions. The temperature range for use in the described processes when combining the reactants together may range from about 15° C. to about 35° C. In some embodiments of the described processes, the temperature when combining the reactants together may range from about 20° C. to about 35° C., from about 20° C. to about 30° C., from about 20° C. to about 25° C., or from about 25° C. to about 35° C.

The following Examples are presented to illustrate various aspects of the methods described herein and should not be construed as limitations to the claims.

EXAMPLES

Example 1. Comparative Method of Preparing Florasulam—One Pot Process (1)

To a 1 L jacketed reactor equipped with condenser was added sulfonyl chloride (SC) (577.08 g in methylene chloride at 14.13 wt %) followed by propylene glycol (PG, 23.2 g) and 2,6-difluoroaniline (2,6-DFA, 39.4 g, 1:1:1 equivalent ratio with SC). Triethylamine (Et₃N, 2:1 equivalent ratio with SC) was added to the mixture via an addition funnel. The addition of Et₃N caused the solution to boil over and some of the solution was lost. After the addition the mixture was heated to 40° C., stirred using an overhead stirrer (about 300 rpm) and allowed to react for 6 hours. After 6 hour the mixture was cooled to 0° C. Barely any solids were noted in the reaction mixture. The solution was filtered using a coarse grain glass frit Buchner funnel. Some solids were retained. The solids were washed with methanol (9.5:1 equivalent ratio with SC). The mother liquor, wash and product were weighed and retained. The mother liquor and wash were analyzed for florasulam via HPLC. Overall, less than 1% yield of the desired product was obtained. Significant amount of the sulfonic acid was formed in the reaction.

Example 2. Comparative Method of Preparing Florasulam—One Pot Process (2)

Example 1 was repeated, but the Et₃N was added slowly to avoid the large exotherm. Mainly sulfonic acid obtained. Less than 1% yield of desired product detected.

Example 3. Method of Preparing Florasulam

To a solution of 3.87 grams (0.03 mol) of 2,6-difluoroaniline in 5.4 grams of propylene glycol was added a solution of 5.73 grams (0.02 mol) of 8-fluoro-5-methoxy[1,2,4]triazolo[1,5-c]pyrimidine-2-sulfonyl chloride (SC) in 7 grams of methylene chloride over 1 hour. The SC solution was added in about 0.5 mL portions every 5-10 minutes. The temperature of the resulting mixture was maintained at less than 25° C. during the addition of the SC. After stirring the reaction mixture for another 1 hour at room temperature, 2.20 grams (0.02 mol) of triethylamine was added over 2.45 hours using a syringe pump. The reaction mixture was stirred at room temperature overnight and then was diluted with 5 g of water over 15 minutes. The resulting mixture was cooled to about 5° C. with an ice bath and then filtered. The collected white solid was rinsed with 15 mL of 7:3 (v/v) methanol-water and then dried at 50° C. to provide 5.44 g (74%) of florasulam (97.7 wt %). An additional 5% yield (total yield 79%) of florasulam was detected in the aqueous filtrate.

What is claimed:

1. A method of preparing florasulam (compound I)

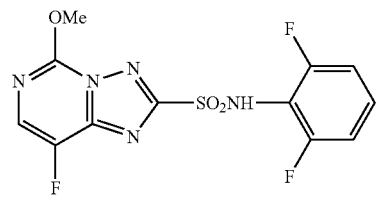

comprising:
a) controlled adding of sulfonyl chloride III

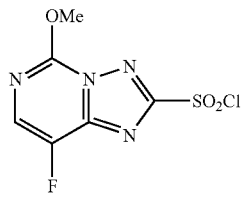

to 2,6-difluoroaniline over a period of at least 1 hour while maintaining a temperature during the adding of 15° C. to 35° C. to form a mixture; and
b) controlled adding of a base to the mixture formed in step a) over a period of at least 0.5 hours while maintaining a temperature during the adding of 15° C. to 30° C.

2. The method of claim 1, further comprising combining the 2,6-difluoroaniline with a glycol solvent prior to adding the sulfonyl chloride III.

3. The method of claim 2, wherein the glycol solvent is 1,2-propylene glycol.

4. The method of claim 1, wherein the mole ratio of 2,6-difluoroaniline to sulfonyl chloride III is from about 1:1 to about 2:1.

5. The method of claim 1, wherein the mole ratio of the base to sulfonyl chloride III is from about 0.5:1 to about 2:1.

6. The method of claim 1, wherein the base is selected from a trialkylamine, or a heterocylic amine.

7. The method of claim 6, wherein the trialkylamine is triethylamine.

8. The method of claim 6, wherein the heterocylic amine is pyridine.

9. A method of preparing florasulam (compound I)

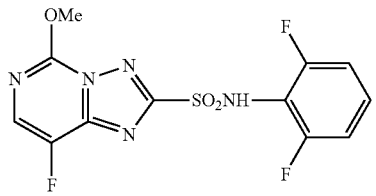

comprising:
a) controlled adding of sulfonyl chloride III

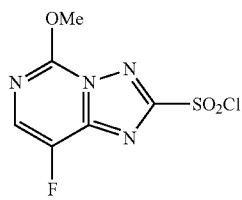

to 2,6-difluoroaniline over a period of at least 1 hour while maintaining a temperature during the adding of 15° C. to 30° C. to form a mixture; and
b) controlled adding of a base to the mixture formed in step a) over a period of at least 0.5 hours while maintaining a temperature during the adding of 15° C. to 30° C.

10. The method of claim 9, further comprising combining the 2,6-difluoroaniline with 1,2-propylene glycol prior to adding the sulfonyl chloride III.

11. The method of claim 9 wherein the mole ratio of 2,6-difluoroaniline to sulfonyl chloride III is from about 1:1 to about 2:1.

12. The method of claim 11, wherein the mole ratio of the base to sulfonyl chloride III is from about 0.5:1 to about 2:1.

13. The method of claim 9, wherein the base is selected from triethylamine or pyridine.

14. A method of preparing florasulam (compound I)

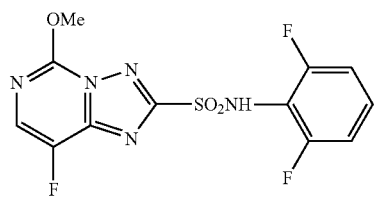

comprising:
a) controlled adding of sulfonyl chloride III

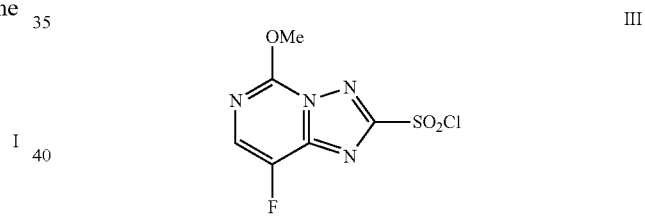

to 2,6-difluoroaniline over a period of at least 1 hour while maintaining a temperature during the adding of 20-25° C. to form a mixture; and
b) controlled adding of a base to the mixture formed in step a) over a period of at least 1 hour while maintaining the temperature during the adding of 20-25° C.

15. The method of claim 14, further comprising combining the 2,6-difluoroaniline with 1,2-propylene glycol prior to adding the sulfonyl chloride III.

16. The method of claim 14 wherein the mole ratio of 2,6-difluoroaniline to sulfonyl chloride III is from about 1:1 to about 2:1.

17. The method of claim 14, wherein the mole ratio of the base to sulfonyl chloride III is from about 0.5:1 to about 2:1.

18. The method of claim 14, wherein the base is selected from triethylamine or pyridine.

* * * * *